US005545653A

United States Patent [19]
Miller et al.

[11] Patent Number: 5,545,653
[45] Date of Patent: Aug. 13, 1996

[54] ANTI-VIRAL COMPOUNDS

[75] Inventors: Shawn C. Miller; Frantz Victor; Wayne A. Spitzer, all of Indianapolis; Thomas R. Sattelberg, Sr., Bloomington; Mark J. Tebbe, Indianapolis, all of Ind.

[73] Assignee: Eli Lilly and Company, Indianapolis, Ind.

[21] Appl. No.: 482,041

[22] Filed: Jun. 7, 1995

[51] Int. Cl.$^6$ ............ A61K 31/415; A61K 31/425; C07D 417/04; C07D 235/30

[52] U.S. Cl. .......... 514/388; 514/370; 548/181; 548/307.4; 548/307.7

[58] Field of Search ............ 514/266.8, 234.5, 514/322, 363, 370, 388, 394, 395; 548/137, 181, 304.7, 306.1, 307.4, 307.7, 308.1, 308.4, 308.7, 309.1, 309.7, 310.1; 544/53, 139; 546/199

[56] References Cited

U.S. PATENT DOCUMENTS 4,118,742  10/1978  Baget et al. .......... 548/304.7
4,492,708   1/1985  Spitzer ................ 548/307.4

Primary Examiner—Patricia L. Morris
Attorney, Agent, or Firm—Janet T. McClain; David E. Boone

[57] ABSTRACT

The present application provides a series of benzimidazole compounds which inhibit the growth of picornaviruses, such as rhinoviruses, enteroviruses, cardioviruses, polioviruses, coxsackieviruses of the A and B groups, echo virus and Mengo virus. Such compounds are also useful as intermediates for preparing additional benzimidazole antiviral compounds.

19 Claims, No Drawings

ANTI-VIRAL COMPOUNDS

BACKGROUND OF THE INVENTION

The incidence of viral upper respiratory disease, the common cold, is immense. It has been estimated that nearly a billion cases annually appear in the United States alone. Rhinovirus, a member of the picornaviridae family, is the major cause of the common cold in humans. Because more than 110 strains of rhinoviruses have been identified, the development of a practical rhinovirus vaccine is not feasible, and chemotherapy appears to be the more desirable approach. Another member of the picornavirus family is the enterovirus, which includes approximately eighty human pathogens. Many of these enteroviruses cause cold-like symptoms; others can cause more serious diseases such as polio, conjunctivitis, aseptic meningitis and myocarditus.

Illness related to rhinovirus infection is evidenced by nasal discharge and obstruction. Furthermore, it has been implicated in otitis media, predisposes the development of bronchitis, exacerbates sinusiris, and has been implicated in the precipitation of asthmatic altoclis. Although it is considered by many to be a mere nuisance, its frequent occurrence in otherwise healthy individuals and the resulting economic importance in terms of employee absenteeism and physician visits have made it the subject of extensive investigation.

The ability of chemical compounds to suppress the growth of viruses in vitro may be readily demonstrated using a virus plaque suppression East or a cytopathic effect test (CPE). Cf Siminoff, Applied Microbiology, 9(1), 66 (1961). Although a number of chemical compounds that inhibit picornaviruses such as rhinoviruses have been identified, many are unacceptable due to 1) limited spectrum of activity, 2) undesirable side effects or 3) inability to prevent infection or illness in animals or humans. See *Textbook of Human Virology*, edited by Robert B. Belshe, chapter 16, "Rhinoviruses," Roland A. Levandowski, 391–405 (1985). Thus, despite the recognized therapeutic potential associated with a rhinovirus inhibitor and the research efforts expended thus far, a viable therapeutic agent has not yet emerged. For example, antiviral benzimidazole compounds have been disclosed in U.S. patent Ser. Nos. 4,008,243, 4,018,790, 4,118,573, 4,118,742 and 4,174,454.

Accordingly, it is a primary object of this invention to provide novel benzimidazole compounds which inhibit the growth of picornaviruses, such as rhinoviruses (bovine and human), enteroviruses such as polioviruses, coxsackieviruses of the A and B groups, or echo virus, cardioviruses such as encephalomyocarditis virus (EMC), and apthoviruses such as foot and mouth disease virus.

SUMMARY OF THE INVENTION

The present invention provides compounds of formula I

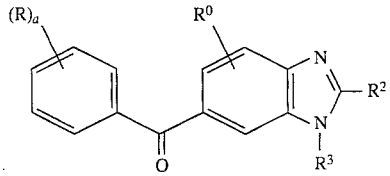

wherein:
a is 1, 2, 3, 4 or 5;

each R is independently hydrogen, hydroxy, thiol, halo, cyano, cyano($C_1$–$C_4$)alkyl, halo($C_1$–$C_4$)alkyl, nitro, amino, $C_1$–$C_4$ alkylamino, di($C_1$–$C_4$)alkylamino, azido, carboxy, $C_1$–$C_6$ alkyl, $C_2$–$C_6$ alkenyl, carbamoyl, carbamoyloxy, carbamoylamino, N-($C_1$–$C_4$)alkylcarbamoyl, —$OCF_3$, —$OCCl_3$, N,N-di($C_1$–$C_4$)alkylcarbamoyl, $C_1$–$C_4$ alkoxy, $C_1$–$C_4$ alkoxycarbonyl, $C_1$–$C_4$ alkoxycarbonyloxy, $C_1$–$C_4$ alkoxycarbonylamino, formyl, $C_2$–$C_4$ alkanoyl, formyloxy, $C_2$–$C_4$ alkanoyloxy, formylamino, $C_2$–$C_4$ alkanoylamino, $C_1$–$C_4$ alkylthio, $C_1$–$C_4$ alkylsulfinyl or $C_1$–$C_4$ alkylsulfonyl;

$R^0$ is hydrogen, halo, $C_1$–$C_4$ alkyl or $C_1$–$C_4$ alkoxy;

$R^2$ is hydrogen, amino, —NHC(O) ($C_1$–$C_6$ alkyl) or —$NHSO_2$ ($C_1$–$C_6$ alkyl);

$R^3$ is $C_1$–$C_6$ alkyl, phenyl, substituted phenyl, furyl, thienyl, thiazol-2-yl, 2-acetamido-4-methyl-thiazol-5yl, 1,3,4-thiadiazol-2-yl, 2-methyl-1,3,4-thiadiazol-5-yl, 2-methylamino-1,3,4-thiadiazol-5-yl, —$NR^5R^6$, —$SO_2$—$R^4$ or a group of the formula:

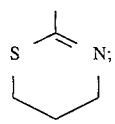

$R^4$ is dimethylamino, $C_1$–$C_6$ alkyl, halo ($C_1$–$C_6$) alkyl, $C_3$–$C_7$ cycloalkyl, phenyl, substituted phenyl or trifluoromethyl; and $R^5$ and $R^6$ are taken together with the nitrogen atom to which they are attached to form pyrrolidino, piperidino or morpholino; provided that when a is 1; then R cannot be hydrogen, $C_1$–$C_6$ alkyl, $C_1$–$C_4$ alkoxy, chloro, bromo, iodo, nitro or trifluoromethyl; or a pharmaceutically acceptable salt thereof.

The present invention also provides pharmaceutical formulations comprising a compound of the present invention, or a pharmaceutically acceptable salt thereof, in combination with a pharmaceutically acceptable carrier, diluent or excipient therefor.

The present invention also provides a method for inhibiting a picornavirus comprising administering to a host in need thereof, an effective amount of a compound of formula I, or a pharmaceutically acceptable salt thereof, wherein a, R, $R^0$, $R^2$ and $R^3$ are as defined above.

DETAILED DESCRIPTION OF THE INVENTION

The present invention relates to benzimidazole compounds of formula I, as described above, that are useful as antiviral agents. Such compounds are also useful for preparing additional antiviral compounds such as various vinyl acetylene benzimidazole compounds.

All temperatures stated herein are in degrees Celsius (°C.). All units of measurement employed herein are in weight units except for liquids which are in volume units.

As used herein, the term "$C_1$–$C_6$ alkyl" represents a straight or branched alkyl chain having from one to six carbon atoms. Typical $C_1$–$C_6$ alkyl groups include methyl, ethyl, propyl, isopropyl, butyl, isobutyl, sec-butyl, t-butyl, pentyl, neo-pentyl, hexyl and the like. The term "$C_1$–$C_6$ alkyl" includes within its definition the term "$C_1$–$C_4$ alkyl."

The term "$C_2$–$C_6$ alkenyl" represents a straight or branched alkenyl chain having from two to six carbon atoms. Typical $C_2$–$C_6$ alkenyl groups include ethenyl, prop-1-enyl, isopropenyl, but-2-enyl, isobut-1-enyl, sec-but-2-enyl, pent-4-enyl, pent-1-enyl, hex-3-enyl and the like.

"Halo" represents chloro, fluoro, bromo or iodo.

"Halo($C_1$–$C_4$)alkyl" represents a straight or branched alkyl chain having from one to four carbon atoms with 1, 2 or 3 halogen atoms attached to it. Typical halo($C_1$–$C_4$)alkyl groups include chloromethyl, 2-bromoethyl, 1-chloroisopropyl, 3-fluoropropyl, 3-bromobutyl, 3-chloroisobutyl, iodo-t-butyl, trichloromethyl, trifluoromethyl, 2,2-chloro-iodoethyl, 2,3-dibromopropyl and the like.

"Cyano($C_1$–$C_4$)alkyl" represents a straight or branched alkyl chain having from one to four carbon atoms with a cyano moiety attached to it. Typical cyano($C_1$–$C_4$)alkyl groups include cyanomethyl, cyanomethyl, 2-cyanoethyl, 1-cyanoisopropyl, 3-cyanopropyl, 3-cyanobutyl, cyano-t-butyl and the like.

"$C_1$–$C_4$ alkylthio" represents a straight or branched alkyl chain having from one to four, carbon atoms attached to a sulfur atom. Typical $C_1$–$C_4$ alkylthio groups include methylthio, ethylthio, propylthio, isopropylthio, butylthio and the like.

"$C_1$–$C_4$ alkoxy" represents a straight or branched alkyl chain having from one to four carbon atoms attached to an oxygen atom. Typical $C_1$–$C_4$ alkoxy groups include methoxy, ethoxy, propoxy, isopropoxy, butoxy and the like.

"$C_1$–$C_4$ alkoxycarbonyl" represents a straight or branched alkoxy chain having from one to four carbon atoms attached to a carbonyl moiety. Typical $C_1$–$C_4$ alkoxy-carbonyl groups include methoxycarbonyl, ethoxycarbonyl, propoxycarbonyl, isopropoxycarbonyl, butoxycarbonyl and the like.

"$C_1$–$C_4$ alkoxycarbonyloxy" represents a straight or branched alkoxy chain having from one to four carbon atoms attached to a carbonyloxy moiety. Typical $C_1$–$C_4$ alkoxycarbonyloxy groups include methoxycarbonyloxy, ethoxycarbonyloxy, propoxycarbonyloxy, isopropoxycarbonyloxy, butoxycarbonyloxy and the like.

"$C_1$–$C_4$ alkoxycarbonylamino" represents a straight or branched alkoxy chain having from one to four carbon atoms attached to a carbonylamino moiety. Typical $C_1$–$C_4$ alkoxycarbonylamino groups include methoxycarbonylamino, ethoxycarbonylamino, propoxycarbonylamino, isopropoxycarbonylamino, butoxycarbonylamino and the like.

"$C_1$–$C_4$ alkylamino" represents a straight or branched alkyl chain having from one to four carbon atoms attached to an amino group. Typical $C_1$–$C_4$ alkylamino groups include methylamino, ethylamino, propylamino, isopropylamino, butylamino, sec-butylamino and the like.

"Di($C_1$–$C_4$)alkylamino" represents two straight or branched alkyl chains having from one to four carbon atoms attached to a common amino group. Typical di($C_1$–$C_4$)alkylamino groups include dimethylamino, ethylmethylamino, methylpropylamino, ethylisopropylamino, butylmethylamino, secbutylethylamino and the like.

"N-($C_1$–$C_4$)alkylcarbamoyl" represents a straight or branched alkyl chain having from one to four carbon atoms attached to the nitrogen atom of a carbamoyl moiety. Typical N-($C_1$–$C_4$)alkylcarbamoyl groups include N-methylcarbamoyl, N-ethylcarbamoyl, N-propylcarbamoyl, N-isopropylcarbamoyl, N-butylcarbamoyl and N-t-butylcarbamoyl and the like.

"$C_2$–$C_4$ alkanoyl" represents a represents a straight or branched alkyl chain having from one to three carbon atoms attached to a carbonyl moiety. Typical $C_2$–$C_4$ alkanoyl groups include ethanoyl, propanoyl, isopropanoyl, butanoyl and the like.

"$C_2$–$C_4$ alkanoylony" represents a straight or branched alkyl chain having from one to three carbon atoms attached to a carbonyloxy moiety. Typical $C_2$–$C_4$ alkanoyloxy groups include ethanoyloxy, propanoyloxy, isopropanoyloxy, butanoyloxy and the like.

"$C_2$–$C_4$ alkanoylamino" represents a straight or branched alkyl chain having from one to three carbon atoms attached to a carbonylamino group. Typical $C_2$–$C_4$ alkanoylamino groups include ethanoylamino, propanoylamino, isopropanoylamino, butanoylamino and the like.

"$C_1$–$C_4$ alkylsulfinyl" represents a straight or branched alkyl chain having from one to four carbon atoms attached to a sulfinyl moiety. Typical $C_1$–$C_4$ alkylsulfinyl groups include methylsulfinyl, ethylsulfinyl, propylsulfinyl, isopropylsulfinyl, butylsulfinyl and the like.

"$C_1$–$C_4$ alkylsulfonyl" represents a straight or branched alkyl chain having from one to four carbon atoms attached to a sulfonyl moiety. Typical $C_1$–$C_4$ alkylsulfonyl groups include methylsulfonyl, ethylsulfonyl, propylsulfonyl, isopropylsulfonyl, butylsulfonyl and the like.

"Substituted phenyl" represents a phenyl ring substituted with halo, $C_1$–$C_4$ alkyl, $C_1$–$C_4$ alkoxy or trifluoromethyl.

As mentioned above, the invention includes the pharmaceutically acceptable salts of the compounds defined by formula I. Although generally neutral, a compound of this invention can possess a sufficiently acidic, a sufficiently basic, or both functional groups, and accordingly react with any of a number of inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a mineral or organic acid or an inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like.

Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

Preferred compounds of this invention are those compounds where:

a is 1, 2 or 3;

each R is independently hydrogen, halo, $C_1$–$C_4$ alkyl, $C_1$–$C_4$ alkoxy, $C_1$–$C_4$ alkylthio, $C_1$–$C_4$ alkylsulfinyl, $C_1$–$C_4$ alkylsulfonyl, trifluoromethyl, di ($C_1$–$C_4$) alkylamino or —$OCF_3$;

$R^0$ is hydrogen, halo or $C_1$–$C_4$ alkyl;

$R^2$ is amino;

$R^3$ is thiazol-2-yl, phenyl, substituted phenyl or —$SO_2$— $R_4$;

$R_4$ is $C_1$–$C_4$ alkyl, di($C_1$–$C_4$)alkylamino or phenyl; or a pharmaceutically acceptable salt thereof.

Of these preferred compounds, more preferred are those compounds of formula I where:

a is 1 or 2;

each R is independently hydrogen, fluoro, methyl, ethyl, methoxy, ethoxy, methylthio, methylsulfinyl, methylsulfonyl or dimethylamino;

$R^0$ is hydrogen;

$R^3$ is thiazol-2-yl, phenyl or —$SO_2$—$R_4$; or a pharmaceutically acceptable salt thereof.

Of these preferred compounds, more preferred are those compounds of the formula:

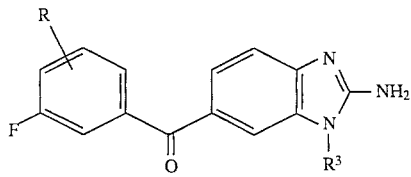

I''' where:

R is independently hydrogen, fluoro, methyl, ethyl, methoxy, ethoxy, methylthio, methylsulfinyl, methylsulfonyl or dimethylamino;

$R^3$ is —$SO_2$–$CH(CH_3)_2$ or —$SO_2$—$N(CH_3)_2$; or a pharmaceutically acceptable salt thereof.

Of these compounds, the most preferred compounds are:

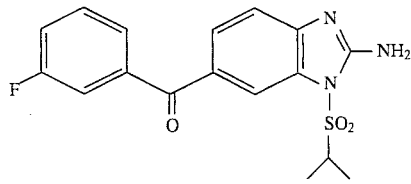

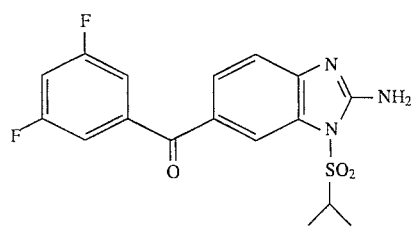

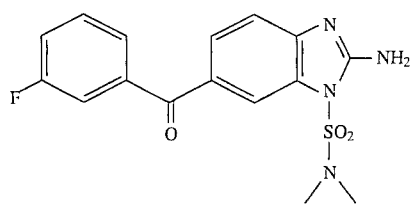

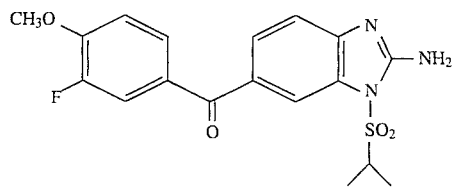

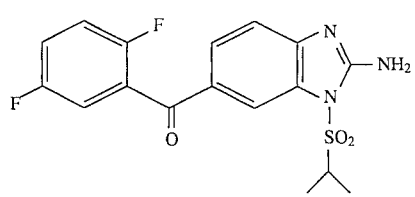

or a pharmaceutically acceptable salt thereof.

The compounds of the formula I may be prepared according to procedures detailed in the art. For example, the ketone compounds may be prepared substantially as described in Paget et al,, U.S. Pat. No. 4,118,742, herein incorporated by reference. In general, Paget et al. describes the preparation of such ketone compounds by ring closing a 3,4-diaminobenzophenone followed by reaction with a sulfonyl halide to provide the desired compounds.

In addition, the compounds of formula I may be prepared according to the following Reaction Scheme II.

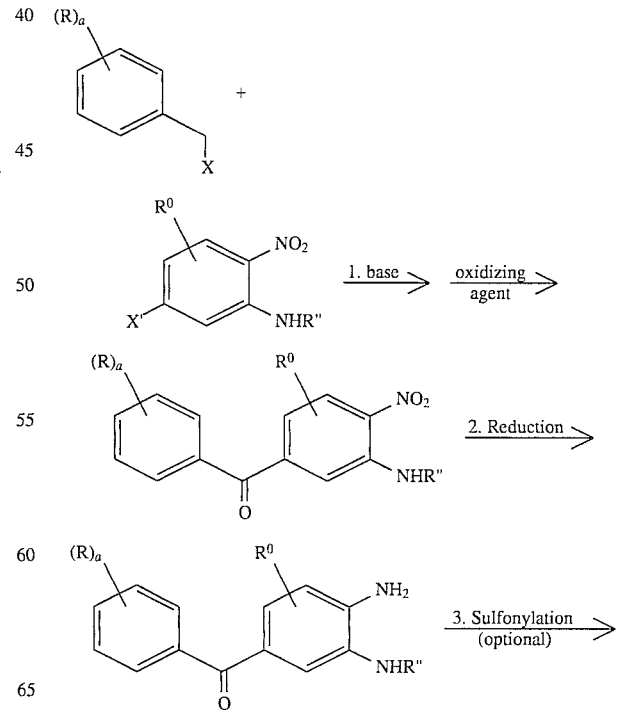

Reaction Scheme II

-continued
Reaction Scheme II

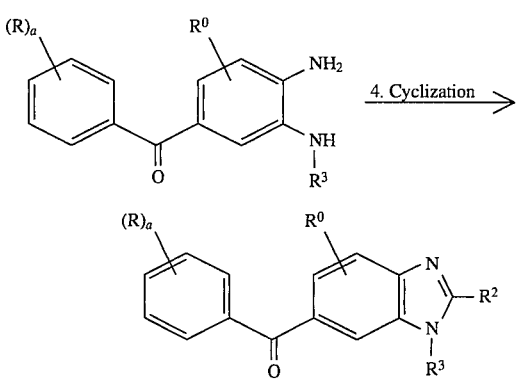

where:
X is cyano or —COOR', where R' is $C_1$–$C_4$ alkyl;
X' is halo;
R" is hydrogen, $C_1$–$C_6$ alkyl, phenyl or substituted phenyl; and
a, R, $R^0$, $R^2$ and $R^3$ are defined above.

Reaction Scheme I, above, is accomplished by carrying out reactions 1–4. Once a reaction is complete, the intermediate compound may be isolated, if desired, by procedures known in the art. For example, the compound may be crystallized and then collected by filtration, or the reaction solvent may be removed by extraction, evaporation or decantation. The intermediate compound may be further purified, if desired, by common techniques such as crystallization or chromatography over solid supports such as silica gel or alumina, before carrying out the next step of the reaction scheme.

Reaction II.1 is accomplished by first exposing an appropriately substituted halo-nitroaniline and an appropriately substituted phenylacetonitrile or benzoate to a base in an organic solvent for one to twenty four hours at a temperature of from about −10° C. to about 40° C. to provide a ketone precursor. The reaction is typically carried out using equimolar proportions of the reactants in the presence of two equivalents of the base. Typical bases include sodium hydride, potassium t-butoxide, lithium diisopropylamide (LDA). A preferred base is potassium t-butoxide. Examples of solvents suitable for use in this reaction include dimethylformamide, dimethylacetamide and the like. Solvent choice is not critical so long as the solvent employed is inert to the ongoing reaction and the reactants are sufficiently solubilized to effect the desired reaction. The ketone precursor is generally prepared in from about one to fifteen hours when the reaction is initiated at 0° C. and allowed to progress at room temperature. The ketone precursor is preferably oxidized in the same reaction mixture without prior isolation or purification.

In particular, the ketone precursor is reacted with an oxidizing agent for thirty minutes to fifteen hours at a temperature of from about 0° C. to about 30° C. to provide the corresponding ketone compound. Typical oxidizing agents include hydrogen peroxide, oxygen and air. The oxygen and air are typically bubbled through the reaction mixture. A preferred oxidizing agent is hydrogen peroxide, preferably in a 30% solution. The ketone is generally prepared in from about thirty to five hours when the reaction is carried out between 0° C. and room temperature. The reaction is preferably monitored by TLC, for example, to ensure that the reaction goes to completion.

In reaction II.2, the nitro substituent on the ketone is reduced according to procedures known in the art to provide the corresponding diaminobenzophenone compound. For example, the nitro substituent may be reduced by catalytic hydrogenation, for example by combining the ketone isolated from reaction II.1 with hydrogen gas in ethanol or tetrahydrofuran and a catalyst. A preferred catalyst is palladium-on-carbon or Raney nickel. Solvent choice is not critical so long as the solvent employed is inert to the ongoing reaction and the nitro reactant is sufficiently solubilized to effect the desired reaction. The hydrogen gas is typically used at a pressure of up to 60 psi, preferably at or about 30 psi. The reaction is generally substantially complete after about 1 to 24 hours when conducted at a temperature in the range of from about 0° C. to about 40° C. The reaction is preferably conducted at a temperature in the range of from about 20° C. to about 30° C. for about 2 to 5 hours.

In reaction II.3, the diaminobenzophenone compound isolated from reaction II.2 where R" is hydrogen may be sulfonylated with an appropriately substituted sulfonyl halide of the formula $R_4$—$SO_2$-halide substantially in accordance with the procedure detailed above to provide the corresponding sulfonamido benzophenone compounds.

In reaction II.4, the compound isolated from reaction II.3 is cyclized via a nitrile intermediate by first exposing the sulfonamido benzophenone compound to a base in an alcoholic solvent such as isopropanol followed by reaction with cyanogen bromide. Typically, the sulfonamido benzophenone and base are reacted at a temperature of from about 0° C. to about 30° C. A preferred base is sodium hydroxide, preferably added in the form of an aqueous solution (about 1–4M). When the sulfonamido benzophenone is completely dissolved, the resultant solution is combined with cyanogen bromide. The cyanogen bromide is typically added in the form of a solution (3–7M for example in acetonitrile). The reaction is generally complete after one to eighteen hours when the reaction mixture is stirred at room temperature. However, in certain instances nitrile intermediate will precipitate out of the reaction mixture within ten to twenty minutes of the initiation of the reaction. In order to form the desired ketone, this precipitate is isolated and then refluxed in an alcoholic solvent such as isopropanol for one to four hours to provide the desired ketone compound of formula I.

The compounds of the formula:

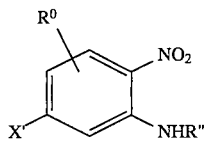

where:
X' and $R^0$ are as defined above; and
R" is $C_1$–$C_6$ alkyl, phenyl or substituted phenyl; used in reaction II.1, above, to prepare compounds of formula I where $R^3$ is $C_1$–$C_6$ alkyl, phenyl or substituted phenyl are prepared by displacing the chloro or fluoro substituent on a compound of the formula

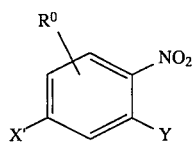

where Y is chloro or fluoro, with the proviso that Y cannot be chloro when X' is fluoro, with a primary amine of the formula $NH_2R^3$, where $R^3$ is $C_1$–$C_6$ alkyl, phenyl or substituted phenyl, in an organic solvent. The reaction is optionally carried out in the presence of an acid scavenger such as potassium carbonate or a large excess of the primary amine. Typical solvents include tetrahydrofuran, dimethylformamide, dimethylacetamide and the like. The reaction is generally complete in one to twenty hours when carried out at a temperature of from about 20° C. to about 80° C. The resultant alkylated halo nitroaniline is then reacted as described in Reaction Scheme II, above.

The compounds of formula I where $R^2$ is —NHC(O)($C_1$–$C_6$ alkyl) or —NHSO$_2$($C_1$–$C_6$ alkyl), may be prepared by acylating or sulfonylating a compound of formula I, where $R^2$ is amino, according to procedures known in the art. For example, the amine compound may be acylated with a suitable acyl halide, isocyanate or chloroformate, preferably in the presence of an acid scavenger such as a tertiary amine, preferably triethylamine. A preferred acylating agent is acetic anhydride. The reaction is typically carried out at a temperature of from about –20° C. to about 25° C. Typical solvents for this reaction include ethers and chlorinated hydrocarbons, preferably diethylether, chloroform or methylene chloride. The amine may be sulfonylated by reaction with a suitably substituted sulfonylating agent in an aprotic solvent. Typical sulfonylating agents include appropriately substituted sulfonyl halides or sulfonic acid anhydrides. A preferred sulfonylating agent is the sulfonyl chloride of the formula ($C_1$–$C_6$ alkyl)—SO$_2$–$C_1$ The reaction is typically carried out at a temperature from about –30° C. to about 50° C. in an aprotic solvent such as tetrahydrofuran. The amine reactant is generally employed in equimolar proportions relative to the acylating or sulfonylating reactant, and preferably in the presence of equimolar quantities of an acid scavenger such as a tertiary amine. A preferred acid scavenger for this reaction is N-methylmorpholine (NMM).

The compounds employed as initial starting materials in the synthesis of the compounds of this invention are known in the art, and, to the extent not commercially available are readily synthesized by standard procedures commonly employed in the art.

It will be understood by those in the art that in performing the processes described above it may be desirable to introduce chemical protecting groups into the reactants in order to prevent secondary reactions from taking place. Any amine, alcohol, alkylamine or carboxy groups which may be present on the reactants may be protected using any standard amino- or carboxy-protecting group which does not adversely affect the remainder of the molecule's ability to react in the manner desired. The various protective groups may then be removed simultaneously or successively using methods known in the art.

The pharmaceutically acceptable salts of the invention are typically formed by reacting a compound of formula I with an equimolar or excess amount of acid or base. The reactants are generally combined in a mutual solvent such as diethyl ether or benzene, for acid addition salts, or water or alcohols for base addition salts. The salts normally precipitate out of solution within about one hour to about ten days and can be isolated by filtration or other conventional methods.

The following Preparations and Examples further illustrate specific aspects of the present invention. It is to be understood, however, that these examples are included for illustrative purposes only and are not intended to limit the scope of the invention in any respect and should not be so construed.

In the following Preparations and Examples, the terms melting point, nuclear magnetic resonance spectra, electron impact mass spectra, field desorption mass spectra, fast atom bombardment mass spectra, infrared spectra, ultraviolet spectra, elemental analysis, high performance liquid chromatography, and thin layer chromatography are abbreviated "m.p.", "NMR", "EIMS", "MS(FD)", "MS(FAB)", "IR", "UV", "Analysis", "HPLC", and "TLC", respectively. The MS(FD) data is presented as the mass number unless otherwise indicated. In addition, the absorption maxima listed for the IR spectra are only those of interest and not all of the maxima observed.

In conjunction with the NMR spectra, the following abbreviations are used: "s" is singlet, "d" is doublet, "dd" is doublet of doublets, "t" is triplet, "q" is quartet, "m" is multiplier, "dm" is a doublet of multiplets and "br.s", "br.d", "br.t", and "br.m" are broad singlet, doublet, triplet, and multiplet respectively. "J" indicates the coupling constant in Hertz (Hz). Unless otherwise noted, NMR data refers to the free base of the subject compound.

The NMR spectra were obtained on a Brüker Corp. 270 MHz instrument or on a General Electric QE-300 300 MHz instrument. The chemical shifts are expressed in delta δ values (parts per million downfield from tetramethyl-silane). The MS(FD) spectra were taken on a Varion-MAT 731 Spectrometer using carbon dendrite emitters. EIMS spectra were obtained on a CEC 21-110 instrument from Consolidated Electrodynamics Corporation. IR spectra were obtained on a Perkin-Elmer 281 instrument. UV spectra were obtained on a Cary 118 instrument. TLC was carried out on E. Merck silica gel plates. Melting points are uncorrected.

EXAMPLE 1

A. 3-Amino-4-nitro-4'-fluorobenzophenone

To a cold (0° C.) solution of 17.25 g (100 mmol) of 5-chloro-2-nitroaniline and 12 ml (100 mmol) of 4-fluorophenylacetonitrile in 200 ml of dimethylformamide, was added 22.44 g (200 mmol) of potassium t-butoxide, under nitrogen. The resultant reaction mixture was warmed to room temperature and reacted overnight. When the reaction was substantially complete, as indicated by TLC (eluent of 40% ethyl acetate in hexane), the reaction mixture was cooled to 0° C. followed by the addition of 30 ml of hydrogen peroxide. When the reaction was substantially complete, as indicated by TLC (eluent of 40% ethyl acetate in hexane), the reaction mixture was poured into 1 liter of 1N hydrochloric acid (aqueous) which resulted in the formation of a yellow/orange precipitate. This precipitate was isolated by filtration. Yield: 23.3 g (89%).

B. 3,4-Diamino-4'-fluorobenzophenone

To a solution of 21 g of the subtitled compound of Example 1A in 250 ml of tetrahydrofuran and 250 ml of ethanol, was added 3.0 g of Raney Nickel catalyst. The resultant reaction mixture was stirred overnight under 30 psi of hydrogen (gas) and then filtered. The resultant filtrate was concentrated in vacuo to provide a yellow solid which was used without further purification.

C. 4-Amino-3-isopropylsulfonamido-4'-fluorobenzophenone

To a solution of 18.14 g (79 mmol) of the subtitled compound of Example 1B in 160 ml of anhydrous methylene chloride and 32 ml of anhydrous pyridine, was added 13.25 ml (118 mmol) of isopropylsulfonylchloride. The resultant reaction mixture was reacted at room temperature for approximately five hours, under nitrogen. When the reaction was substantially complete, as indicated by TLC (eluent of ethyl acetate), the reaction mixture was poured into 400 ml of 1N hydrochloric acid (aqueous). The resulting mixture was diluted with 300 ml of ethyl acetate and the resulting layers were separated, the organic layer dried over magnesium sulfate, filtered and concentrated in vacuo to provide a dark red gum. This gum was purified using Preparatory HPLC (gradient eluent of 30–60% ethyl acetate in hexane). The fractions containing the desired compound were combined and dried in vacuo to provide 17.11 g of a yellow gum that was used without further purification. Yield: 65%

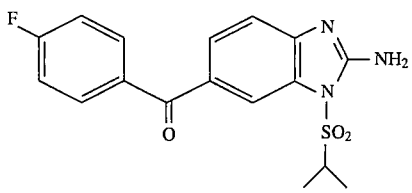

D.

To a solution of 17.11 g (51 mmol) of the subtitled compound of Example 1C and 25 ml of 2N sodium hydroxide (aqueous) in 100 ml of isopropanol, was added 10 ml of a 5M cyanogen bromide. The resultant reaction mixture was reacted at room temperature for approximately thirty minutes resulting in the formation of a precipitate. This precipitate was isolated by filtration to provide 11.68 g of a solid. This solid was resuspended in 250 ml of isopropanol and the resultant mixture was refluxed until all of the material had dissolved and then cooled to provide 10.0 g of the desired subtitled compound (crystals). Yield: 55%. Analysis for $C_{17}H_{16}FN_3O_3S$: Calcd: C, 56.50; H, 4.46; N, 11.63; Found: C, 56.71; H, 4.48; N, 11.82. MS (FD): 361.

$^1$H NMR (300 MHz; d6 -DMSO ): δ1.32 ( d, J=7 Hz, 6H) ; 3.96 (septet, J=7.0 Hz, 1H); 7.34–7.44 (m, 5H); 7.63 (dd, J=1,6 8.3 Hz, 1H); 7.79–7.83 (m, 2H); 7.95 (d, J=1.5 Hz, 1H).

EXAMPLE 2

A. 4-Amino-3-isopropylsulfonamido-4'-di(methyl)aminobenzophenone

A solution of 2 g of the subtitled compound of Example 1C, 2 g of potassium carbonate and 100 ml of anhydrous dimethylamine was reacted for approximately sixteen hours at 120° C. The reaction mixture was then dried in vacuo to provide a residue. This residue was suspended in a mixture of ethyl acetate and 1N hydrochloric acid (aqueous). The desired subtitled compound was isolated from the organic layer and used without further purificaton.

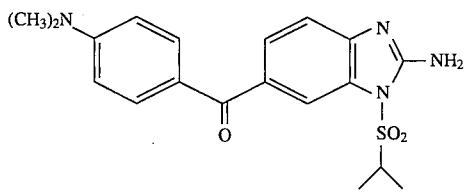

B.

To a cold solution (0° C.) containing 35.64 g (98.6 mmol) of the subtitled compound of Example 3A, 400 ml of isopropanol and 50 ml of 2N sodium hydroxide (aqueous), was added 19.8 ml of a 5M cyanogen bromide solution (98.6 mmol). The resultant reaction mixture was warmed to room temperature resulting in the formation of a tan precipitate. This precipitate was isolated by filtration, washed with diethyl ether and then dried in vacuo. Yield: 28.8 g (76%). MS (FD): 386.

$^1$H NMR (300 MHz; $d_6$-DMSO): δ1.25 (d, 6H); 3.05 (s, 6H); 3.90 (m, 1H); 6.80 (d, 2H); 7.25–7.85 (m, 7H).

EXAMPLE 3

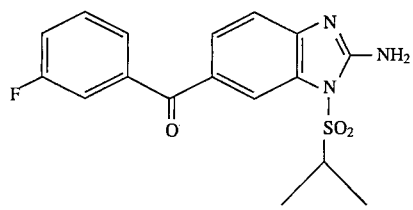

The titled compound was prepared substantially in accordance with the procedure detailed in Examples 1A–D. MS (FD): 361.2.

$^1$H NMR (300 MHz; $d_6$-DMSO): δ1.25 (d, 6H); 3.95 (m, 1H); 7.25–7.70 (m, 6H); 7.95 (s, 1H);

IR (CHCl$_3$): ν 3397, 3016, 1640, 1604, 1588, 1541, 1443, 1387, 1361, 1284, 1271, 1155, 1044, 840 cm$^{-1}$.

The following compounds were prepared substantially in accordance with the procedure detailed in Example 1A–D.

EXAMPLE 4

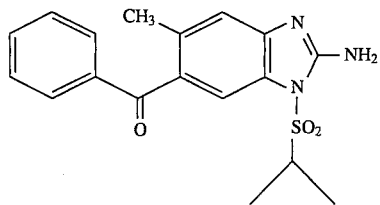

MS (FD): 357.
$^1$H NMR (300 MHz; $d_6$-DMSO): δ1.36 (d, J=6.7 Hz, 6H); 2.38 (s, 3H); 3.60 (septet, J=6.7 Hz, 1H); 6.50 (br. s, 2H); 7.25 (d, J=4.7 Hz, 1H); 7.45 (m, 1H); 7.57 (m, 2H); 7.78 (m, 2H).
IR (CHCl$_3$): ν 3398, 2985, 1645, 1608, 1361, 1279 cm$^{-1}$.

EXAMPLE 5

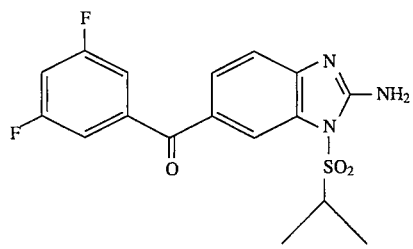

Analysis for $C_{17}H_{15}F_2N_3O_3S$: Calcd: C, 53.82; H, 3.99; N, 11.08; Found: C, 53.63; H, 3.90; N, 11.03. MS (FD): 379.3.

$^1$H NMR (300 MHz; $d_6$-DMSO): δ1.30 (d, 6H); 3.95 (m, 1H); 7.31–7.65 (m, 7H); 7.95 (s, 1H);

IR (CHCl$_3$): ν 3507, 3397, 2982, 1640, 1594, 1541, 1442, 1361, 1324, 1266, 1155, 1124, 1045, 989 cm$^{-1}$.

EXAMPLE 6

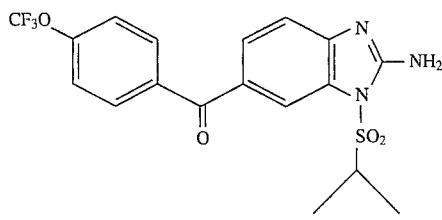

MS (FD): 427.

$^1$H NMR (300 MHz; d$_6$-DMSO): δ1.25 (d, 6H); 3.95 (m, 1H); 7.28 (d, 1H); 7.44 (s, 2H); 7.50–7.65 (m, 4H); 7.82 (d, 1H); 7.95 (s, 1H);

IR (CHCl$_3$): ν 3507, 3397, 2982, 1640, 1604, 1541, 1443, 1387, 1361, 1262, 1174, 1156, 1134, 1044, 920 cm$^{-1}$.

EXAMPLE 7

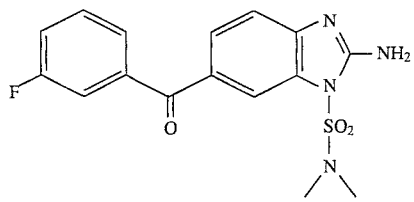

MS (FD): 362.1.

$^1$H NMR (300 MHz; d$_6$-DMSO): δ2.95 (s, 6H); 7.31-7.75 (m, 8H); 7.95 (s, 1H).

IR (CHCl$_3$): ν 3504, 3461, 3397, 2977, 1637, 1603, 1586, 1538, 1445, 1390, 1285, 1170, 1053, 970, 840 cm$^{-1}$.

EXAMPLE 8

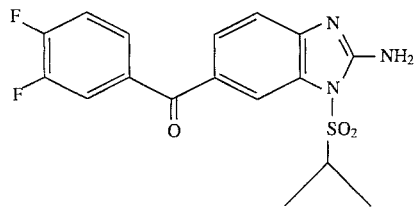

Analysis for C$_{17}$H$_{15}$F$_2$N$_3$O$_3$S: Calcd: C, 53.82; H, 3.99; N, 11.08; Found: C, 53.63; H, 4.05; N, 11.33.

MS (FD): 379.1.

$^1$H NMR (300 MHz; d$_6$-DMSO): δ1.30 (d, J=2.4 Hz, 6H); 3.95 (septet, J=2.4 Hz, 1H); 7.35 (d, J=2.5 Hz, 1H); 7.46 (s, 2H); 7.56–7.80 (m, 3H); 7.75–7.85 (m, 1H); 7.94 (s, 1H).

IR (CHCl$_3$): ν 3480, 1649.4, 1599.2, 1545.2, 1512.4, 1360, 1312.7, 1290, 1180.6, 1120.8, 1046.5, 584.6 cm$^{-1}$.

UV/VIS λ$_{max}$=321.5 nm (E=15637); 248.0 nm (E=13856); 211.5 nm (E=27821).

EXAMPLE 9

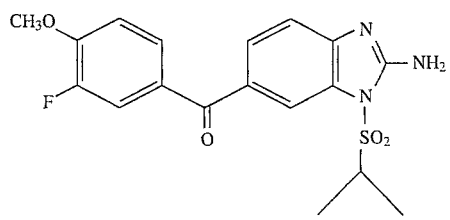

Analysis for C$_{18}$H$_{18}$FN$_3$O$_4$S: Calcd: C, 55.23; H, 4.63; N, 10.73; Found: C, 55.12; H, 4.65; N, 10.53.

MS(FD): 391.2.

$^1$H NMR (300 MHz; d$_6$-DMSO): δ1.29 (d, J=2.2 Hz, 6H); 3.93 (septet, J=2.2, 1H); 7.95 (s, 3H); 7.28–7.38 (m, 2H); 7.52–7.64 (m, 3H); 7.90 ( s, 1H).

IR (CHCl$_1$): ν 3397.1, 1639.7, 1608.8, 1579.9, 1542.3, 1518.2, 1442, 1279 cm$^{-1}$.

UV/VIS λ$_{max}$318 nm (E=22070); 247 nm (E=12107); 211 nm (E=31784).

EXAMPLE 10

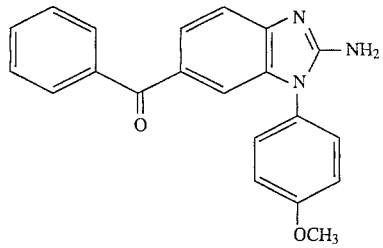

Analysis for C$_{21}$H$_{17}$N$_3$O$_2$: Calcd: C, 73.45; H, 4.99; N, 12.24; Found: C, 73.31; H, 5.08; N, 12.11.

MS (FD): 343.

$^1$H NMR (300 MHz; CDCl$_3$): δ3.90 (s, 3H); 5.19 (s, 2H); 7.07–7.83 (m, 12H).

IR (CHCl$_3$): ν 3506.1, 3406.7, 3012.2, 1631, 1610.7, 1526.9, 1515.2, 1454.5, 1274.4, 1254.8, 1219.2, 836.3 cm$^{-1}$.

UV/VIS λ$_{max}$=330 nm (E=17200); 213 nm (E=35900).

EXAMPLE 11

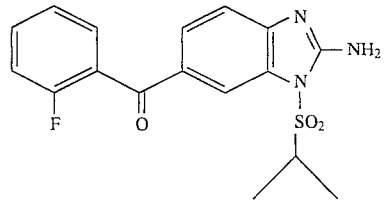

Analysis for C$_{17}$H$_{16}$FN$_3$O$_3$S: Calcd: C, 56.50; H, 4.46; N, 11.63; S, 8.82; Found: C, 56.61; H, 4.49; N, 11.52; S, 8.70.

MS (FD): 361.

$^1$H NMR ( 300 MHz; d$_6$-DMSO ): δ1.30 (d, 6H); 3.95 (m, 1H); 7.20–7.70 (m, 8H); 7.98 (s, 1H).

EXAMPLE 12

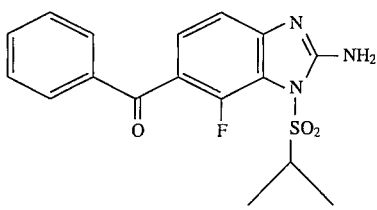

MS (FD: 361.
¹H NMR (300 MHz; CDCl₃): δ1.44 (d, J=6.9 Hz, 6H); 3.68 (septet, J=6.9, 1H); 6.26 (s, 2H); 7.29 (m, 2H); 7.48 (m, 2H); 7.61 (m, 1H); 7.85 (dd, J=1.0, 6.8, 2H).

EXAMPLE 13

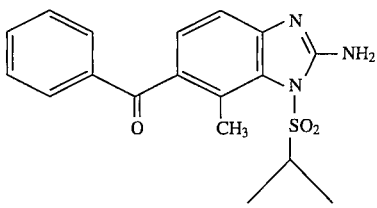

MS (FD): 357.
¹H NMR (300 MHz; d₆-DMSO): δ1.32 (d, J=6.6 Hz, 6H); 2.34 (s, 3H); 3.92 septet, J=6.6 Hz, 1H); 7.02 (d, J=8.5 Hz, 1H); 7.12 (m, 2H); 7.44 (d, J=8.5 Hz, 1H); 7.56 (m, 2H); 7.73 (m, 3H)

EXAMPLE 14

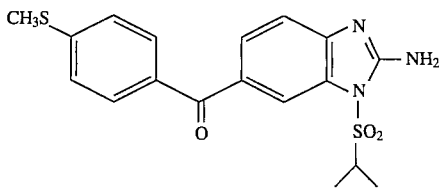

Analysis for C₁₈H₁₉N₃O₃S: Calcd: C, 55.51; H, 4.92; N, 10.79; S, 16.46; Found: C, 55.60; H, 4.63; N, 10.58; S, 16.22.
MS(FD): 389

EXAMPLE 15

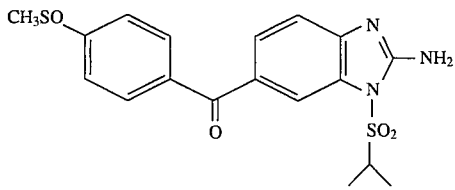

MS (FD): 405.
¹H NMR (300 MHz; d₆-DMSO): δ1.30 (d, 6H); 2.82 (s, 3H); 3.96 (m, 1H); 7.30–7.70 (m, 8H); 7.98 (s, 1H).

EXAMPLE 16

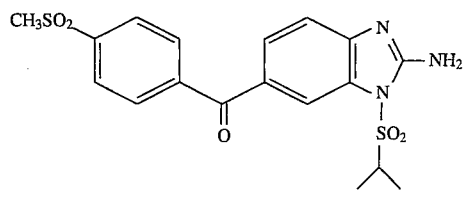

MS (FD): 421.
¹H NMR (300 MHz; d₆-DMSO): δ1.30 (d, 6H); 3.35 (S, 3H); 3.95 (m, 1H); 7.30–8.20 (m, 9H).

EXAMPLE 17

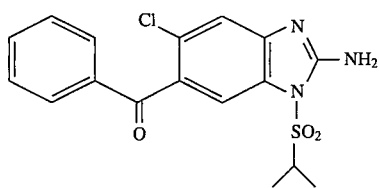

MS (FD): 377.
¹H NMR (300 MHz; d₆-DMSO): δ1.75 (d, 6H); 3.90 (m, 1H); 7.40–7.90 (m, 9H).

EXAMPLE 18

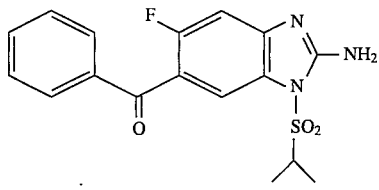

Analysis for C₁₇H₁₆FN₃O₃S: Calcd: C, 56.50; H, 4.46; N, 11.63; S, 8.87; Found: C, 56.70; H, 4.72; N, 11.78; S, 8.81.
MS(FD): 361.
¹H NMR (300 MHz; d₆-DMSO): δ1.30 (d, 6H); 3.95 (m, 1H); 7.10–7.80 (m, 9H).

EXAMPLE 19

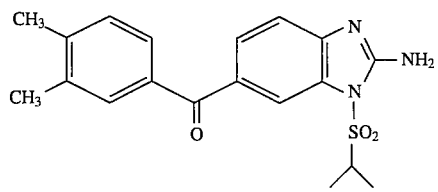

Analysis for C₁₉H₂₁N₃O₃S: Calcd: C, 61.44; H, 5.70; N, 11.31; S, 8.63; Found: C, 61.06; H, 5.92; N, 11.14; S, 8.54.
MS (FD): 371.
¹H NMR (300 MHz; d₆-DMSO): δ1.30 (d, 6H); 2.29 (s, 3H); 2.31 (s, 1H); 3.92 (m, 1H); 7.20–7.65 (m, 7H); 7.90 (s, 1H).

EXAMPLE 20

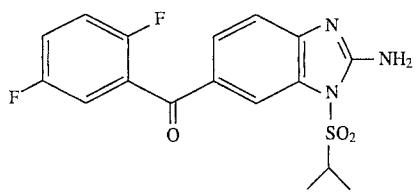

MS (FD): 379.

$^1$H NMR (300 MHz;CDCl$_3$): δ1.41 (d, 6H); 3.70 (m, 1H); 6.60 (s, 2H); 7.10–7.30 (m, 3H); 7.35 (d, 1H); 7.72 (d, 1H); 8.18 (s, 1H).

As noted above, the compounds of the present invention are useful as antiviral agents. They have shown inhibitory activity against various enterovirus and rhinovirus. An embodiment of the present invention is a method of treating or preventing picornaviridae infection comprising administering to a host in need thereof an effective amount of a compound of formula I or a pharmaceutically acceptable salt thereof.

The term "effective amount" as used herein, means an amount of a compound of formula I which is capable of inhibiting viral replication. The picornaviridae inhibition contemplated by the present method includes either therapeutic or prophylactic treatment, as appropriate. The specific dose of compound administered according to this invention to obtain therapeutic or prophylactic effects will, of course, be determined by the particular circumstances surrounding the case, including, for example, the compound administered, the route of administration, the condition being treated and the individual being treated. A typical daily dose will contain a dosage level of from about 0.01 mg/kg to about 50 mg/kg of body weight of an active compound of this invention. Preferred daily doses generally will be from about 0.05 mg/kg to about 20 mg/kg and ideally from about 0.1 mg/kg to about 10 mg/kg.

The compounds can be administered by a variety of routes including oral, rectal, transdermal, subcutaneous, intravenous, intramuscular and intranasal. The compounds of the present invention are preferably formulated prior to administration. Therefore, another embodiment of the present invention is a pharmaceutical formulation comprising an effective amount of a compound of formula I or a pharmaceutically acceptable salt thereof and a pharmaceutically acceptable carrier, diluent or excipient therefor.

The active ingredient in such formulations comprises from 0.1% to 99.9% by weight of the formulation. By "pharmaceutically acceptable" it is meant that the carrier, diluent or excipient is compatible with the other ingredients of the formulation and not deleterious to the recipient thereof.

The present pharmaceutical formulations are prepared by known procedures using well-known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for example, up to 10% by weight of the active compound, soft and hard gelatin capsules, suppositories, sterile injectable solutions, sterile packaged powders and the like.

The following formulation examples are illustrative only and are not intended to limit the scope of the invention in any way. The term "active ingredient" means a compound according to formula I or a pharmaceutically acceptable salt thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

|  | Quantity (mg/capsule) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight |
| --- | --- |
| Active ingredient | 0.25 |
| Methanol | 25.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

|  | Quantity (mg/tablet) |
|---|---|
| Active ingredient | 60 |
| Starch | 45 |
| Microcrystalline cellulose | 35 |
| Polyvinylpyrrolidone (as 10% solution in water) | 4 |
| Sodium carboxymethyl starch | 4.5 |
| Magnesium stearate | 0.5 |
| Talc | 1 |
| Total | 150 |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

|  | Quantity (mg/capsule) |
|---|---|
| Active ingredient | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| Active ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 mL dose, are made as follows:

| Active ingredient | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active ingredient | 100 mg |
|---|---|
| Isotonic saline | 1,000 ml |

The solution of the above ingredients generally is administered intravenously to a subject at a rate of 1 mL per minute.

The following experiment was carried out to demonstrate the ability of the compounds of formula I to inhibit certain virus.

Test Method

African green monkey kidney cells (BSC-1) or Hela cells (5-3) were grown in 25 cc Falcon flasks at 37° C. in medium 199 with 5 percent inactivated fetal bovine serum (FBS), penicillin (150 units 1 ml) and streptomycin (150 micrograms per milliliter (µg/ml)). When confluent monolayers were formed, the supernatant growth medium was removed and 0.3 mL of an appropriate dilution of virus (echo, Mengo, Coxsackie, polio or rhinovirus) were added to each flask. After absorption for one hour at room temperature, the virus infected cell sheet was overlaid with a medium comprising one part of 1 percent Lonagar No. 2 and one part double strength medium 199 with FBS, penicillin and streptomycin which contains drug at concentrations of 100, 50, 25, 12, 6, 3 and 0 µg/ml. The flask containing no drug served as the control for the test. The stock solutions of vinyl acetylene benzimidazole compounds were diluted with dimethylsulfoxide to a concentration of $10^4$ µg/ml. The flasks were then incubated for 72 hours at 37° C. for polio, Coxsackie, echo and Mengo virus and 120 hours at 32° C. for rhinovirus. Virus plaques were seen in those areas were the virus infected and reproduced in the cells. A solution of 10 percent formalin and 2 percent sodium acetate was added to each flask to inactivate the virus and fix the cell sheet to the surface of the flask. The virus plaques, irrespective of size, were counted after staining the surrounding cell areas with crystal violet. The plaque count was compared to the control count at each drug concentration. The activity of the test compound was expressed as percentage plaque reduction, or percent inhibition. Alternatively, the drug concentration which inhibits plaque formation by 50 percent can be used as a measure of activity. The 50 percent inhibition is indicated by the symbol IC50.

Test results for various compounds of formula I are summarized in Tables 1 and 2, below, by Example Number and indicating the test virus and percent inhibition of plaque reduction which is presented as IC50 (μg/ml). Such IC50 values represents the amount of test compound needed to inhibit 50% of the plaque formation.

TABLE I

| | IC50 (μg/ml) | | |
|---|---|---|---|
| Example No | PV-1 | RhV-14 | CS-21C |
| 3 | | 2.14 | |
| 5 | | 3.9 | |
| 6 | | 0.329 | |
| 11 | 1.7 | | 0.44 |
| 20 | 0.19 | 1.32 | |

PV (poliovirus); RhV (Rhinovirus); CS (Coxsackie virus) the numbers following the virus designation represent particular strains.

We claim:

1. A compound of the formula:

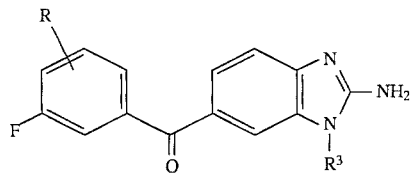

where:
R is independently hydrogen, fluoro, methyl, ethyl, methoxy, ethoxy, methylthio, methylsulfinyl, methylsulfonyl or dimethylamino;
$R^3$ is thiazol-2-yl, phenyl or —$SO_2$—$R_4$ wherein $R_4$ is $C_1$–$C_4$ alkyl, di($C_1$–$C_4$)alkylamino or phenyl;
or a pharmaceutically acceptable salt thereof.

2. A compound according to claim 1 which is:

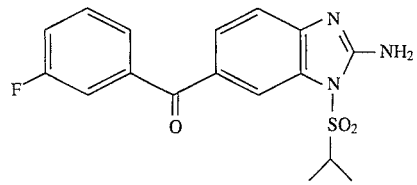

or a pharmaceutically acceptable salt thereof.

3. A compound according to claim 1 which is:

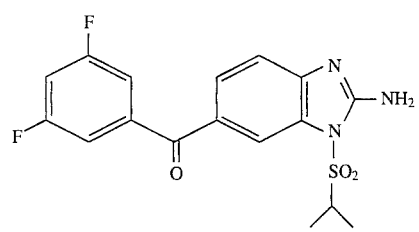

or a pharmaceutically acceptable salt thereof.

4. A compound according to claim 1 which is:

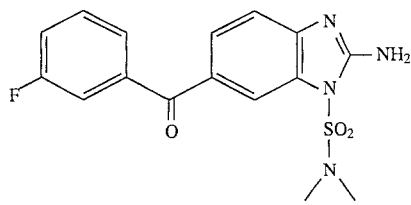

or a pharmaceutically acceptable salt thereof.

5. A compound according to claim 1 which is:

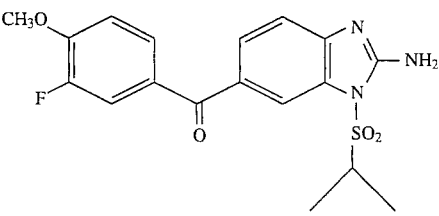

or a pharmaceutically acceptable salt thereof.

6. A compound according to claim 1 which is:

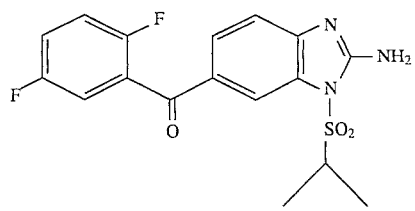

or a pharmaceutically acceptable salt thereof.

7. A pharmaceutical formulation comprising one or more pharmaceutically acceptable carriers, diluents or excipients and a compound of claim 1.

8. A pharmaceutical formulation according to claim 7 where the compound is

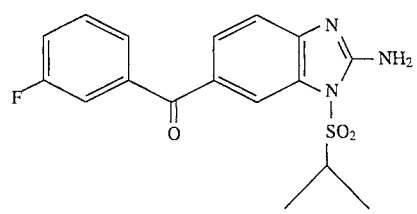

or a pharmaceutically acceptable salt thereof.

9. A pharmaceutical formulation according to claim 7 where the compound is

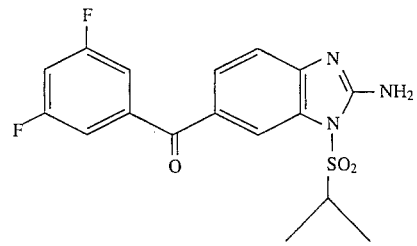

or a pharmaceutically acceptable salt thereof.

10. A pharmaceutical formulation according to claim 7 where the compound is

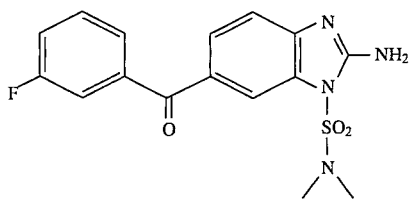

or a pharmaceutically acceptable salt thereof.

11. A pharmaceutical formulation according to claim 7 where the compound is

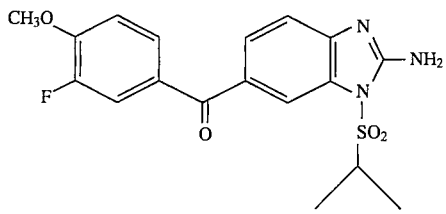

or a pharmaceutically acceptable salt thereof.

12. A pharmaceutical formulation according to claim 7 where the compound is

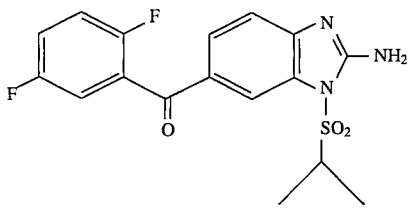

or a pharmaceutically acceptable salt thereof.

13. A method for inhibiting a picornavirus comprising administering to a host in need thereof, an effective amount of a compound of claim 4.

14. A method according to claim 13 where the compound is

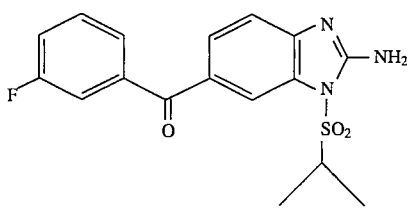

or a pharmaceutically acceptable salt thereof.

15. A method according to claim 13 where the compound is

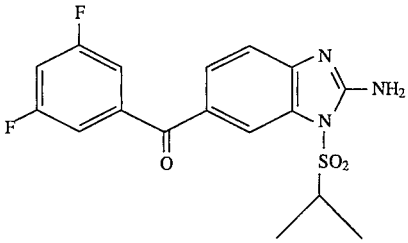

or a pharmaceutically acceptable salt thereof.

16. A method according to claim 13 where the compound is

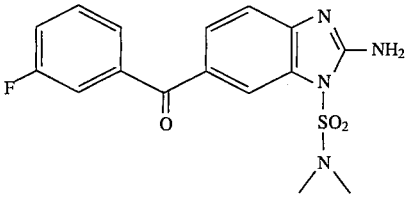

or a pharmaceutically acceptable salt thereof.

17. A method according to claim 13 where the compound is

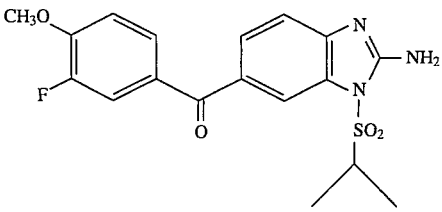

or a pharmaceutically acceptable salt thereof.

18. A method according to claim 13 where the compound is

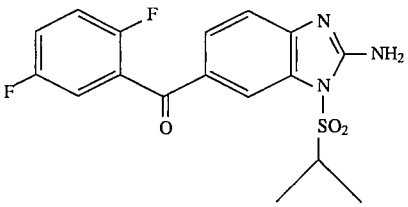

or a pharmaceutically acceptable salt thereof.

19. A method according to claim 13 where the picornavirus is a rhinovirus.

* * * * *

UNITED STATES PATENT AND TRADEMARK OFFICE
CERTIFICATE OF CORRECTION

PATENT NO.   : 5,545,653

DATED        : August 13, 1996

INVENTOR(S)  : S. Miller et al.

It is certified that an error appears in the above-identified patent and that said Letters Patent is hereby corrected as shown below:

Column 1, line 22, delete "sinusiris" and insert --sinusitis-- therefor.

Column 1, line 31, delete "East" and insert --test-- therefor.

Column 9, line 27, delete "SO$_2$-C$_1$" and insert --SO$_2$-Cl-- therefor.

Column 20, line 49, delete "Lonagar" and insert --Ionagar-- therefor.

Column 23, line 43 (Claim 13, line 3), delete "claim 4" and insert --claim 1-- therefor.

Signed and Sealed this

Twelfth Day of November, 1996

Attest:

BRUCE LEHMAN

Attesting Officer

Commissioner of Patents and Trademarks